United States Patent
Komiyama et al.

(10) Patent No.: US 6,476,049 B2
(45) Date of Patent: Nov. 5, 2002

(54) THERAPEUTIC AGENT FOR INTERMITTENT CLAUDICATION

(75) Inventors: Takashi Komiyama, Tokyo; Hideaki Kihara; Ken Hirose, both of Kawasaki; Hiroshi Sigematsu, Chofu; Ryota Yoshimoto, Kawasaki, all of (JP)

(73) Assignee: Ajinomoto Co., Inc., Tokyo (JP)

( * ) Notice: Subject to any disclaimer, the term of this patent is extended or adjusted under 35 U.S.C. 154(b) by 0 days.

(21) Appl. No.: 09/933,908

(22) Filed: Aug. 22, 2001

(65) Prior Publication Data

US 2002/0037906 A1 Mar. 28, 2002

Related U.S. Application Data

(63) Continuation of application No. PCT/JP00/01046, filed on Feb. 24, 2000.

(30) Foreign Application Priority Data

Feb. 26, 1999 (JP) .......................... 11-050150

(51) Int. Cl.[7] ................. A61K 31/4545; C07D 401/12
(52) U.S. Cl. ...................................... 514/316; 546/189
(58) Field of Search ........................... 514/316; 546/189

(56) References Cited

U.S. PATENT DOCUMENTS 5,932,593 A * 8/1999 Makino et al. ............. 514/316

FOREIGN PATENT DOCUMENTS

| EP | 0 682 015 | 11/1995 |
| WO | WO98/37888 | 9/1998 |
| WO | WO00/51604 | 8/2000 |

OTHER PUBLICATIONS

Chemical Abstracts, vol. 121, No. 13, Sep. 26, 1994; 32945 (1993).
Chemical Abstracts. vol. 131, No. 12, Sep. 20, 1999, 605802 (1999), 360769 (1999), 317391 (1999) and 402310 (1998).
Chemical Abstracts, vol. 131, No. 17, Oct. 25, 1999, 605802 (1999) and 360769 (1999).

* cited by examiner

Primary Examiner—Charanjit S. Aulakh
(74) Attorney, Agent, or Firm—Oblon, Spivak, McClelland, Maier & Neustadt, PC.

(57) ABSTRACT

A compound 1-formyl-N-(2-(4-(5H-dibenzo[a,d]cyclohepten-5-ylidene)-1-piperidinyl)) ethyl isonipecotic acid amide or an analog thereof or a pharmaceutically acceptable salt thereof provides a therapeutic agent for treating a patient suffering from intermittent claudication.

7 Claims, 1 Drawing Sheet

THERAPEUTIC AGENT FOR INTERMITTENT CLAUDICATION

This application is a Continuation of PCT/JP00/01046 filed Feb. 24, 2000, now WO00/51604.

BACKGROUND OF THE INVENTION

The present invention relates to a drug for treating a patient suffering from intermittent claudication and more specifically to a drug for treating a patient suffering from intermittent claudication caused by, in particular, peripheral circulatory disorders such as arteriosclerosis obliterans or thromboangiitis obliterans.

The intermittent claudication means a symptom in which the following two conditions are repeated: the difficulty of continuous walking due to the malaise and pains of the lower limb muscles caused after the locomotion of a constant distance and the alleviation of these symptoms or a condition ready for walking again after the rest for several minutes.

One of the causes thereof may be peripheral arterial occlusive disease induced by the vasculopathy such as arteriosclerosis obliterans, thromboangiitis obliterans, aortitis syndrome, Behcet's disease and collagenosis. It would generally be recognized that the amount of blood required for the muscular motion is reduced to a relatively low level due to these peripheral circulatory disorders {the degree of oxygen saturation in tissues (tissue oxygen saturation) is reduced}, metabolites such as lactic acid are accumulated in the muscles to thus stimulate terminals of sensory nerves and thus it becomes difficult to continue walking due to the pain.

As drugs for treating a patient suffering from intermittent claudication, there have conventionally been used, for instance, pentoxifylline having an effect of improving the red blood cell deformability, anti-platelet agents and cilostazol as a vasodilator (the $71^{st}$ American Heart Association in the United States, 1998, Lecture No. 58), but the effects of these drugs have been far from satisfactory.

This is because, there are some problems to be solved, for instance, those relating to methods for evaluating drug efficacy, methods for clinical diagnosis and the efficacy of these drugs. The conventional evaluation methods have relied on the length of the walking distance judged on the basis of the patient's subjective findings, but these methods suffer from such a problem that they are inferior in the objectivity and reproducibility. Moreover, there has been known a method for determining the ratio of the blood pressure observed at the ankle joint to that observed at the brachial region using the Doppler method. However, the ratio is a value observed during the resting stage of a patient and therefore, this method is insufficient as a method for diagnosing the symptoms of the intermittent claudication observed during motions.

On the other hand, as a result of the investigation of patients suffering from intermittent claudication, it has been recognized that there is a good correlation between the oxyhemoglobin-recovery time and the time required for the recovery of the tissue oxygen saturation, which have recently been used, in clinic, for evaluating the efficacy of drugs for treating intermittent claudication and the degree of the seriousness of the disorder (KOMIYAMA Takashi et al., Therapeutic Research, 1996, Vol. 17, No. 4, pp. 213–215).

DISCLOSURE OF THE INVENTION

Accordingly, it is an object of the present invention to provide a drug useful in the treatment of a patient suffering from intermittent claudication and having high safety.

It is another object of the present invention to provide a drug useful for the production of a therapeutic agent for intermittent claudication.

It is a further object of the present invention to provide a method for treating a patient suffering from intermittent claudication.

The present inventors have established an animal model possessing pathema quite similar to that of intermittent claudication in clinic and improved the evaluation method and apparatus, have conducted various studies using the animal model and the method and apparatus, have found that a specific piperidine derivative known as a serotonin antagonist or an antiplatelet agent and disclosed in Japanese Un-Examined Patent Publication No. Hei 8-3135 show extremely high effect as compared with the conventionally known therapeutic agents for intermittent claudication and have thus completed the present invention.

According to an aspect of the present invention, there is thus provided a therapeutic agent for intermittent claudication, which comprises a piperidine derivative represented by the following general formula (1) or a salt thereof as an effective component:

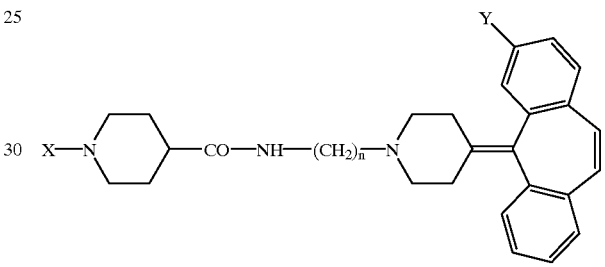

(1)

wherein n is an integer equal to 2 or 3, Y represents a hydrogen atom or a halogen atom, and X represents a formyl group, an acetyl group or a hydrogen atom.

According to another aspect of the present invention, there is provided the use of the foregoing piperidine derivative represented by the general formula (1) or a salt thereof in order to prepare a therapeutic agent for intermittent claudication.

According to a further aspect of the present invention, there is also provided a method for treating a patient suffering from intermittent claudication, which comprises the step of administering, to the patient, an intermittent claudication-remedy comprising, as an effective component, the foregoing piperidine derivative represented by the general formula (1) or a salt thereof.

In this connection, the compound according to the present invention is effective, in particular, when the intermittent claudication is caused due to peripheral circulatory disorders and further when the peripheral circulatory disorder is caused due to arteriosclerosis obliterans. Moreover, particularly effective is a compound of Formula (1) wherein n is 2, Y is a hydrogen atom and X is a formyl group, among others.

BEST MODE FOR CARRYING OUT THE INVENTION

Figure 1:
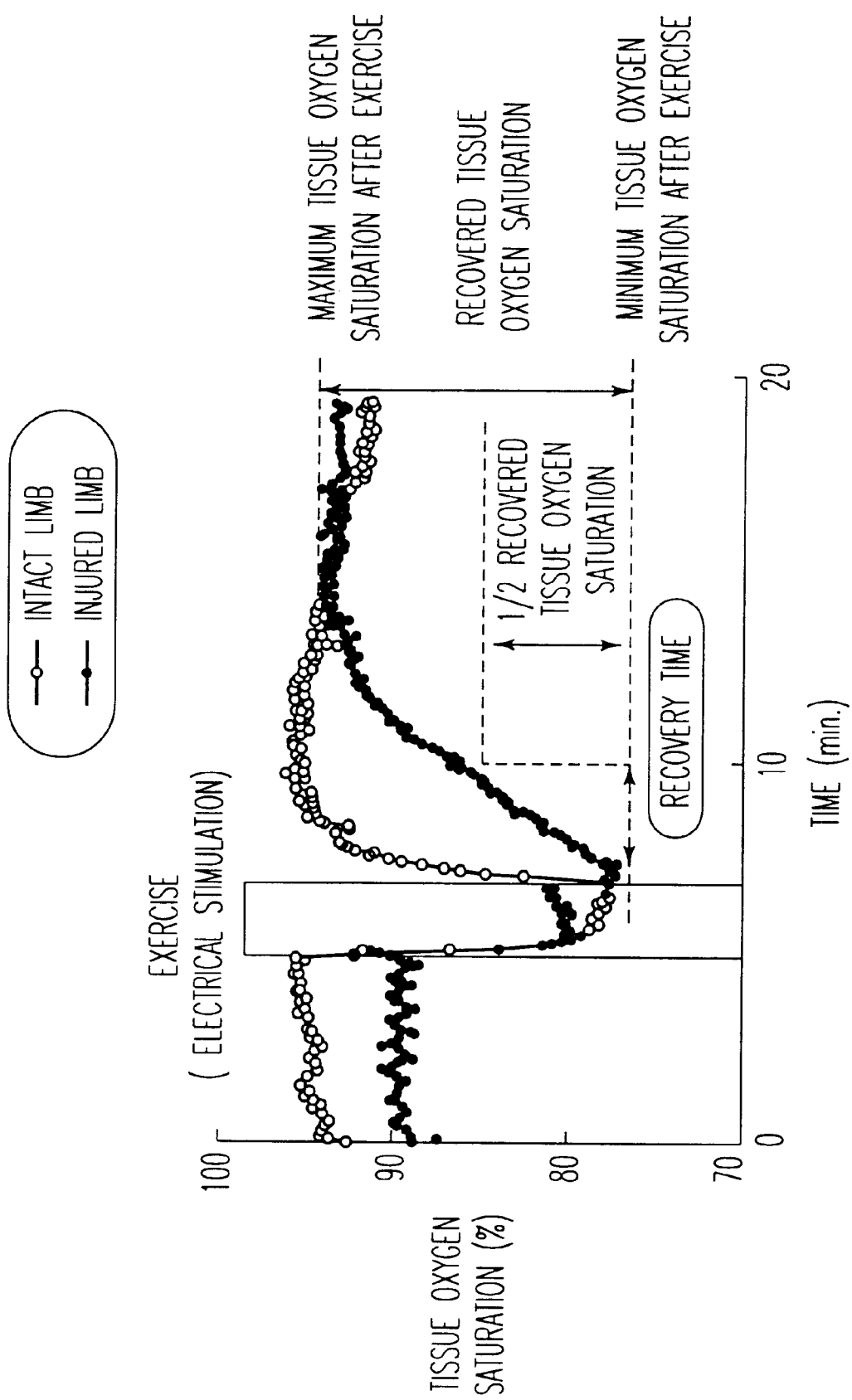
FIG. 1 is a diagram showing the way to obtain the time required for the recovery of the tissue oxygen saturation after the application of an exercise.

The piperidine derivatives represented by the general formula (1) according to the present invention are known ones and can be prepared by, for instance, a method as disclosed in Japanese Un-Examined Patent Publication No. Hei 8-3135. For instance, 1-formyl-N-(2-(4-(5H-dibenzo[a, d]cyclohepten-5-ylidene)-1-piperidinyl))-ethyl-isonipecotic acid amide represented by the following formula (2), which is particularly useful among the foregoing compounds according to the present invention, can be prepared as follows: Di-t-butyl dicarbonate is reacted with 2-aminoethyl bromide hydrobromide in the presence of sodium hydrogen carbonate to give N-t-butoxycarbonyl-2-bromoethylamine. Then the resulting compound is condensed with 4-(5H-dibenzo[a,d]cyclohepten-5-ylidene)piperidine in the presence of a base such as triethylamine to give 4-(5H-dibenzo [a,d]cyclohepten-5-ylidene)-1-(2-t-butoxycarbonylamino) ethyl)piperidine. Further this condensed product is treated with, for instance, 4M-hydrochloric acid/dioxane to remove the t-butoxycarbonyl group and then the product is condensed with 1-formyl isonipecotic acid using a condensation agent such as 1-(3-dimethylaminopropyl)-3-ethylcarbodiimide to thus give a target compound.

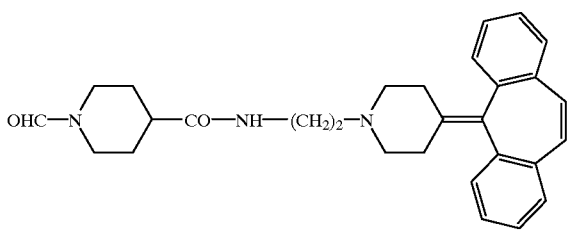

(2)

The compounds prepared by such a method are isolated and purified in the form of the free forms or salts thereof. The isolation and purification can be carried out by a variety of methods such as extraction, concentration, distillation, crystallization as disclosed in Japanese Un-Examined Patent Publication No. Hei 9-176119 and various kinds of chromatography techniques.

In the compounds represented by the general formula (1) according to the present invention, n is preferably 2, and Y is preferably a hydrogen atom. Moreover, X preferably represents a formyl group. In the present invention, particularly preferred compound is one represented by the foregoing formula (2), or a compound represented by the general formula (1) wherein n is 2, Y is a hydrogen atom and X is a formyl group.

As pharmaceutically acceptable salts of the piperidine derivatives according to the present invention, there may be listed, for instance, acid addition salts with mineral acids such as hydrochloric acid, hydrobromic acid, sulfuric acid, nitric acid and phosphoric acid; and organic acids such as formic acid, acetic acid, lactic acid, salicylic acid, mandelic acid, citric acid, oxalic acid, maleic acid, fumaric acid, tartaric acid, tannic acid, malic acid, tosylic acid, methanesulfonic acid, and benzenesulfonic acid.

When using the piperidine derivative or a pharmaceutically acceptable salt thereof according to the present invention as a drug for treating a patient suffering from intermittent claudication, the dosage forms thereof may be, for instance, tablets, powders, pills, granules, sugar-coated tablets, emulsions, capsules, solutions, injections and suppositories. These pharmaceutical preparations may be prepared using carriers, excipients or vehicles and other auxiliary agents currently used in the manufacture of pharmaceuticals according to the usual methods.

The therapeutic agent of the present invention may be administered through either oral or parenteral routes. Moreover, the dose thereof may vary depending on the age, body weight and conditions to be treated of a patient, but the dose for adults generally ranges from 0.01 to 500 mg per day and preferably 0.1 to 50 mg for the oral route, while the dose for adults ranges from 1 μg to 100 mg and preferably 0.01 to 10 mg for the parenteral route. Incidentally, when the compound of the present invention is used as a therapeutic agent for treating a patient suffering from intermittent claudication, the therapeutic agent can effectively be used by administration thereof through, in particular, the oral route.

REFERENCE EXAMPLE 1

Establishment of Rabbit Intermittent Claudication Model

To male New Zealand White Rabbits, there was given 1% cholesterol-containing RC4 (available from ORIENTAL KOBO Co., Ltd.) chow over 4 weeks (100 g/day/animal) to obtain a high cholesterol-loaded group (8 animals), while normal RC4 (available from ORIENTAL KOBO Co., Ltd.) chow was given to a group of such animals (normal feed-loaded group: 6 animals). The groins of these animals belonging to these two groups were incised in their supine position, under the anesthesia with ketamine and xylazine, followed by exposing the right femoral artery and then repeating, three times, the balloon injury treatment, which comprises the steps of inserting a Fogarty's balloon catheter in a length of 7 cm into the artery, expanding the balloon catheter to a diameter of 5 mm within the right iliac artery and then pulling out the catheter while the balloon catheter was still in the expanded state and finally ligating the right femoral artery. After 3 days from the operation, the both gluteal regions and the posterior of the lower limbs were dissected in the supine position of the animal under the anesthesia with ketamine and xylazine. The probe of a near infrared spectrophotometer was directly fitted to the interior of the both side gastrocnemius muscles, followed by application of electrical stimulation at 1 Hz to the sciatic nerves on both sides for 2 minutes as exercise loads.

After the application of exercise, these animals were kept quiet rest, followed by monitoring the process in which the degree of tissue oxygen saturation reduced during exercise was recovered, using an multi-wavelength-type near infrared spectrophotometer to thus obtain the time required for the recovery of the degree of tissue oxygen saturation in the both limbs. As such multi-wavelength-type near infrared spectrophotometer, there was used MCPD-2000 available from OTSUKA ELECTRONICS Co., Ltd., which had been improved in such a manner that the device could almost simultaneously detect the tissue oxygen saturation for the both side gastrocnemius muscles. In this respect, the distance between the light guide and detector of near infrared light rays was set at a level of 5 mm. A ½ recovered tissue oxygen saturation (½ $StO_2$), which was an intermediate value of the tissue oxygen saturation observed after the application of the exercise (the minimum tissue oxygen saturation after exercise) and the tissue oxygen saturation observed after the recovery of exercise (the maximum tissue oxygen saturation after exercise) and then the recovery time was defined to be the time required for arriving at the level of ½ $StO_2$ after the end of exercise-application.

FIG. 1 shows typical examples of the recovery process of the tissue oxygen saturation observed for the injured limbs and the recovery process of the tissue oxygen saturation observed for the intact limbs.

In addition, Table 1 shows the results of the recovery time-determination observed for the right limb (injured limb), which was subjected to the balloon injury treatment and then ligated, and untreated left limb (intact limb) of the high cholesterol-loaded group as well as the results of the recovery time-determination observed for the limb (injured limb) of the normal chow-loaded group, which was subjected to the balloon injury treatment and then ligated.

TABLE 1

| Group | Case | Case (animals) | Recovery Time of Tissue Oxygen Saturation (min) |
|---|---|---|---|
| Normal Chow-Loaded Group | Injured limb | 6 | 1.9 ± 0.55 |
| High Cholesterol Chow-Loaded Group | Injured limb | 8 | 3.8 ± 0.46 |
| High Cholesterol Chow-Loaded Group | Normal limb | 8 | 0.26 ± 0.06 |

The data listed in Table 1 clearly indicate that in the foregoing model, the recovery times of the tissue oxygen saturation in the injured limbs observed for both the high cholesterol chow-loaded group and the normal chow-loaded group are distinctly longer than those observed for the normal limbs. Therefore, it can be recognized that the oxygen dynamics in the tissues can quantitatively and objectively be detected even in this model through the use of this evaluation method.

Moreover, when comparing the recovery times in the injured limbs observed for both the high cholesterol chow-loaded group and the normal chow-loaded group with one another, it was found that the recovery time observed for the high cholesterol chow-loaded group is clearly prolonged. More specifically, it would be considered that a circulatory disorder is caused due to the arteriosclerosis associated with the high cholesterol chow-load and the recovery time is correspondingly extended as compared with that observed for the normal chow-loaded group. Accordingly, the high cholesterol chow-loaded model may be considered to be an objective animal model well reflecting the clinical intermittent claudication. Therefore, this high cholesterol chow-loaded group was used in the following drug-evaluation as an animal model for intermittent claudication.

EXAMPLE 1

To male New Zealand White Rabbits, there was given 1% cholesterol-containing RC4 (available from ORIENTAL KOBO Co., Ltd.) chow over 4 weeks (100 g/day/animal), followed by dividing these animals into two groups in such a manner that the total cholesterol levels in the plasma were identical to one another and then subjecting these two groups to treatments identical to those used in the foregoing model.

To these animals, there was orally administered, once a day, 1-formyl-N-(2-(4-(5H-dibenzo [a, d] cyclohepten-5-ylidene)-1-piperidinyl)) ethyl isonipecotic acid amide represented by the formula (2) after dissolving it in water in an amount of 3 mg/kg over the term extending from the day following the operation to the day on which the near infrared spectrophotometric measurement was initiated. On the other hand, distilled water was orally administered to the control group once a day. After 3 days from the operation, the recovery time of the tissue oxygen saturation after exercise was determined using a near infrared spectrophotometer. The results thus obtained are summarized in the following Table 2.

TABLE 2

| Group | Cases (animals) | Recovery Time of Tissue Oxygen Saturation (min) |
|---|---|---|
| Control Group | 8 | 3.8 ± 0.46 |
| Compound of Formula (2) (3 mg/kg) | 9 | 2.0 ± 0.40 |

COMPARATIVE EXAMPLE 1

The same procedures used in Example 1 were repeated except for using 300 mg/kg of pentoxifylline in place of the compound represented by the formula (2) to thus carry out the determination. The results thus obtained are listed in the following Table 3.

TABLE 3

| Group | Cases (animals) | Recovery Time of Tissue Oxygen Saturation (min) |
|---|---|---|
| Control Group | 6 | 3.8 ± 1.28 |
| Pentoxifyflline (300 mg/kg) | 8 | 7.1 ± 1.65 |

COMPARATIVE EXAMPLE 2

The same procedures used in Example 2 were repeated except for using 100 mg/kg of cilostazol in place of the compound represented by the formula (2) to thus carry out the same determination carried out in Example 2. The results thus obtained are listed in the following Table 4.

TABLE 4

| Group | Cases (animals) | Recovery Time of Tissue Oxygen Saturation (min) |
|---|---|---|
| Control Group | 6 | 2.8 ± 0.97 |
| Cilostazol (100 mg/kg) | 6 | 3.5 ± 0.52 |

COMPARATIVE EXAMPLE 3

The same procedures used in Example 2 were repeated except for using 100 mg/kg of sarpogrelate hydrochloride (J. Med. Chem., 1990, 33:1818) in place of the compound represented by the formula (2) to thus carry out the determination identical to that carried out in Example 2. The results thus obtained are listed in the following Table 5.

TABLE 5

| Group | Cases (animals) | Recovery Time of Tissue Oxygen Saturation (min) |
|---|---|---|
| Control Group | 7 | 3.9 ± 1.08 |
| Sarpogrelate · HCl (300 mg/kg) | 6 | 3.4 ± 1.33 |

The data shown in the foregoing Tables 2, 3, 4 and 5 indicate that the drug of the present invention can significantly reduce the recovery time of the tissue oxygen saturation in the injured limb of the high cholesterol chow-loaded rabbit observed after 3 days from the injury and after the exercise and can improve the oxygen dynamics in the lower limb muscles. Contrary to this, pentoxifylline used as a therapeutic agent for treating a patient suffering from intermittent claudication did not show any reduction in the recovery time even at a dose of 300 mg/kg. In addition, Cilostazol showing superior therapeutic effect as compared with Pentoxifylline can reduce the recovery time as compared with that observed for Pentoxifylline, but does not show any substantial reduction of the recovery time at a dose of 100 mg/kg. Moreover, sarpogrelate hydrochloride, which may be a useful therapeutic agent for intermittent claudication, did not show any reduction of the recovery time even at a dose of 300 mg/kg. Moreover, there was not observed any ischemic necrosis of the lower limbs at all in any animals examined.

These experimental results clearly indicate that in the animal model, which would reflect the clinical intermittent claudication, the drug of the present invention can improve the oxygen dynamics in the lower limb muscles after exercise and possesses an effect of treating a patient suffering from intermittent claudication.

REFERENCE EXAMPLE 2

Establishment of Rat Intermittent Claudication Model

Using an improved model of Corcico et al. (Corcico N. Cardiovasc. Drugs Ther., 1993, 7:241–251), male SD rats were made run on a rat treadmill (available from NATSUME SEISAKUSHO) at a speed of 10 m/min, followed by stepwise raising the running speed by 5 m/min every 3 minutes to thus determine the time (the maximum running time) required till the rats could not run any more and to thus evaluate the running ability of each animal. On the following day, these rats were anesthetized with pentobarbital and then 3.5 mg/ml of sodium laurate solution (available from SIGMA Company; dissolved in a 0.5% glucose aqueous solution) was injected into the right and left femoral arteries at a dose of 100 μl/leg to thus induce artificial intermittent claudication in the animals.

After 1, 3, 7, 14 and 21 days from the injection of the sodium laurate solution, the maximum running time was determined according to the method described above. The results thus obtained are summarized in the following Table 6.

TABLE 6

| Date of Determination | Case No. | Maximum Running Time (sec) |
| --- | --- | --- |
| Prior to Laurate-injection | 5 | 1122 ± 83 |
| 1 Day after the Laurate-injection | 5 | 416 ± 67 |
| 3 Days after the Laurate-injection | 5 | 581 ± 156 |
| 7 Days after the Laurate-injection | 5 | 726 ± 103 |
| 14 Days after the Laurate-injection | 3 | 806 ± 95 |
| 21 Days after the Laurate-injection | 3 | 968 ± 58 |

As will be seen from the data listed in Table 6, the maximum running time or the maximum walking distance observed after the laurate-injection is distinctly reduced as compared with the running ability observed before the laurate-injection. This reduction in the running ability is caused by the peripheral circulatory disorders induced by the thrombosis and the like due to endothelial injury. This would be a model highly objectively reflecting the clinical intermittent claudication since the tissue image is quite similar to thromboangiitis obliterans and the maximum walking distance is significantly reduced. In the establishment of this model, if 100 μl/leg of a 6 mg/ml lauric acid solution is injected into the femoral artery, the lower limbs cause necrosis and slough after one week from the injection and therefore, this is recognized to be an effective model for the reproduction of intermittent claudication.

In this connection, the maximum walking time or the maximum walking distance observed after one day from the laurate injection was shortest and it was improved with the elapse of time, but it was not completely improved even after 21 days from the injection. Moreover, few ischemic necrosis of the lower limb was observed and the asthenia of limbs were detected, but the asthenia was gradually improved.

EXAMPLE 2

The same procedures used in Reference Example 2 were repeated using male SD rats (15 animals) to thus establish a rat intermittent claudication model. On the day following the lauric acid-injection, each animal was inspected for the maximum running time and these animals were divided into three groups so that the running abilities of these groups were almost identical to one another. To the first group (drug-administered group), there was orally administered, once a day, 3 mg/kg of hydrochloride of the compound represented by the formula (2) dissolved in distilled water over the term extending from the day following the lauric acid injection to $21^{st}$ day, while 60 mg/kg of pentoxifylline (available from SIGMA Company) dissolved in distilled water was orally administered to the second group once a day as a comparative example. To the third group (control group), there was orally administered distilled water once a day. After 3, 7, 14 and 21 days from the lauric acid-injection, the maximum running time of each animal was determined to thus evaluate the recovery rate relative to the maximum walking time observed after the day following the lauric acid-injection (this was defined to be 100). In addition, the presence of any lesion on the limbs was simultaneously confirmed. The presence of any lesion on the lower limb was rated according to the following 6 evaluation criteria: 0: normal and all of the 5 toes could widely be opened; 1: limbs could look upward, but the toes could not be opened; 2: the limbs looked downward; 3: not less than 3 claws were necrosed; 4: not less than 3 toes were necrosed; and 5: not less than 3 toes were left out. The results thus obtained are summarized in the following Tables 7 and 8.

TABLE 7

Change of Maximum Walking Time after Lauric Acid Injection with Time

| Group | Cases (animals) | After 1 day | After 3 days | After 7 days | After 14 days | After 21 days |
| --- | --- | --- | --- | --- | --- | --- |
| Control Group | 5 | 100 | 132 ± 18 | 177 ± 18 | 198 ± 25 | 215 ± 34 |
| Compound of Formula (2) (3 mg/kg/day) | 5 | 100 | 189 ± 10 | 256 ± 7 | 252 ± 24 | 317 ± 40 |
| Pentoxifylline (60 mg/kg/day) | 5 | 100 | 178 ± 22 | 189 ± 19 | 211 ± 64 | 249 ± 13 |

TABLE 8

Change, with time, in Score for Lower Limb Lesion

|  | After 1 day | After 3 days | After 7 days | After 14 days | After 21 days |
|---|---|---|---|---|---|
| Control Group | 4.0 | 3.8 | 3.8 | 3.8 | 3.4 |
| Pentoxifylline (60 mg/kg/day) | 4.0 | 3.7 | 3.7 | 3.3 | 2.5 |
| Compound of Formula (2) (3 mg/kg/day) | 4.0 | 3.2 | 2.2 | 1.7 | 1.5 |

As has been shown in Table 7, the group, to which 3 mg/kg of hydrochloride of the piperidine derivative represented by the formula (2) as a drug of the present invention was administered, showed a significant increase of the maximum walking time (the maximum walking time had been reduced after the injection) after 7 days from the lauric acid-injection, as compared with that observed for the control group. On the other hand, the group, to which pentoxifylline was administered, had a tendency of increasing the maximum walking time even at a dose of 60 mg/kg, but the function thereof was not considered to be significant. Moreover, as to the lesions of the lower limbs, the group, to which 3 mg/kg of hydrochloride of the piperidine derivative represented by the formula (2) as a drug of the present invention was administered, showed an effect of preventing the development of any lesion on the lower limbs as compared with the control group. On the other hand, the group, to which pentoxifylline was administered, showed such an effect of preventing the development of any lesion on the lower limbs, but the effect was still insufficient.

The foregoing experimental results clearly indicate that the drug comprising, as an effective component, the hydrochloride of the piperidine derivative according to the present invention permits the improvement of the development of any lesion on lower limbs and the improvement of the maximum walking time or the maximum walking distance and possesses an effect of treating a patient suffering from intermittent claudication. Moreover, pentoxifylline, which has clinically been used as a therapeutic agent for intermittent claudication (although the effect is insufficient), has a tendency of increasing the maximum walking time. On the other hand, the drug of the present invention shows an excellent improving effect as compared with pentoxifylline and accordingly, higher clinical effect can be expected by the use of the drug of the present invention.

The drug comprising the hydrochloride of the piperidine derivative according to the present invention would show therapeutic and prophylactic effects for intermittent claudication in, for instance, intermittent claudication and the peripheral circulatory disorders such as arteriosclerosis obliterans and thromboangiitis obliterans associated with the progress of, for instance, arteriosclerosis (accumulation of cholesterol on the lumen, thrombosis), which are considered to be a cause of the intermittent claudication.

What is claimed is:

1. A method for treating intermittent claudication, comprising administering to a patient suffering from intermittent claudication, a piperidine derivative of formula (1) or pharmaceutically acceptable salt thereof in an amount effective to treat intermittent claudication:

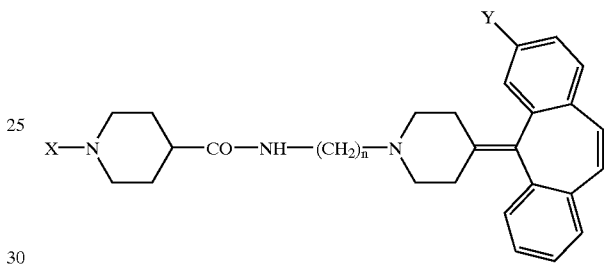

(1)

wherein n is 2 or 3; Y is a hydrogen atom or a halogen atom; and X is a formyl group, an acetyl group, or a hydrogen atom.

2. The method of claim 1, wherein n is 2.

3. The method of claim 1, wherein Y is a hydrogen atom.

4. The method of claim 1, wherein X is a formyl group.

5. The method of claim 1, wherein n is 2; Y is a hydrogen atom; and X is a formyl group.

6. The method of claim 1, wherein the intermittent claudication is caused by a peripheral circulatory disorder.

7. The method of claim 6, wherein the peripheral circulatory disorder is occlusive arteriosclerosis.

* * * * *